United States Patent
Moghbeli et al.

(10) Patent No.: US 10,017,864 B2
(45) Date of Patent: Jul. 10, 2018

(54) AUTOMATED TANK CATHODIC PROTECTION/CORROSION MONITORING SYSTEM

(71) Applicants: Omidreza Moghbeli, Rancho Cucamonga, CA (US); Sebastian Borucki, Corona, CA (US)

(72) Inventors: Omidreza Moghbeli, Rancho Cucamonga, CA (US); Sebastian Borucki, Corona, CA (US)

( * ) Notice: Subject to any disclaimer, the term of this patent is extended or adjusted under 35 U.S.C. 154(b) by 162 days.

(21) Appl. No.: 15/151,933

(22) Filed: May 11, 2016

(65) Prior Publication Data

US 2016/0348255 A1 Dec. 1, 2016

Related U.S. Application Data

(60) Provisional application No. 62/167,696, filed on May 28, 2015.

(51) Int. Cl.
*C23F 13/02* (2006.01)
*C23F 13/22* (2006.01)
*G01N 17/02* (2006.01)

(52) U.S. Cl.
CPC ............ *C23F 13/22* (2013.01); *G01N 17/02* (2013.01)

(58) Field of Classification Search
CPC .......... C23F 13/02; C23F 13/04; C23F 13/06; C23F 13/08; C23F 13/22; C23F 2213/10; C23F 2213/20
See application file for complete search history.

(56) References Cited

U.S. PATENT DOCUMENTS

| | | | | |
|---|---|---|---|---|
| 4,258,323 A | * | 3/1981 | Andrews | G01R 31/02 324/326 |
| 4,581,497 A | * | 4/1986 | Morrison | B65H 75/38 191/12.2 R |
| 5,084,764 A | * | 1/1992 | Day | G01M 3/005 348/84 |
| 5,305,631 A | * | 4/1994 | Whited | C23F 13/04 220/565 |
| 7,159,851 B1 | * | 1/2007 | Ross | B66C 23/48 254/275 |

(Continued)

*Primary Examiner* — Edna Wong
*Assistant Examiner* — Alexander W Keeling
(74) *Attorney, Agent, or Firm* — Kenneth L. Green; Averill & Green

(57) ABSTRACT

An automated tank Cathodic/Corrosion Protection (CCP) monitoring system includes a mobile CCP data collection device. The data collection device can be moved horizontally to different locations in the tank. A reference electrode and corrosion coupon are lowered from the data collection device to desired depths within a liquid medium in the tank to collect data. The data collection device is connected to a programmable, external control unit enabling a operator to program a data collection schedule, the horizontal and vertical distance between readings, interruption of the system if the system is designed in a way to handle interruption, and has the ability to transmit the data remotely to a control center. These capabilities enable automated, remote monitoring of the CCP system, eliminate the safety concerns associated with sending technicians onto tank roofs, and give a more accurate and complete representation of the CCP system functionality and level of protection achieved.

5 Claims, 3 Drawing Sheets

(56) References Cited

U.S. PATENT DOCUMENTS

| | | | |
|---|---|---|---|
| 8,327,963 B1* | 12/2012 | Faulkingham | B62B 5/0076 |
| | | | 180/167 |
| 2007/0035315 A1* | 2/2007 | Hilleary | C23F 13/22 |
| | | | 324/700 |

* cited by examiner

AUTOMATED TANK CATHODIC PROTECTION/CORROSION MONITORING SYSTEM

CROSS-REFERENCE TO RELATED APPLICATIONS

The present application claims the priority of U.S. Provisional Patent Application Ser. No. 62/167,696 filed May 28, 2015, which application is incorporated in its entirety herein by reference.

BACKGROUND OF THE INVENTION

The present invention relates generally to a system and apparatus for automated tank cathodic protection/corrosion monitoring. More specifically, the present invention is an automated tank cathodic protection/corrosion monitoring system.

Internal, submerged, metallic surfaces of liquid-containing tanks and reservoirs are subject to corrosion due to electrochemical reactions between the metallic surfaces and the liquid medium they are in contact with. Cathodic protection systems are installed in tanks and reservoirs to limit the amount of corrosion occurring on submerged metallic surfaces of the tanks and reservoirs. Tank and reservoir owners/operators often monitor the performance of the cathodic protection system and the level of corrosion protection achieved from the cathodic protection system in order to verify the system's functionality and ensure the submerged metallic structures are properly protected from corrosion.

The cathodic protection systems in tanks are monitored by measuring the potential of the tank utilizing a high impedance voltmeter with respect to a reference electrode employed within the liquid medium. The potential measurement is representative of the condition of the submerged, metallic surfaces within a close vicinity of the location of the reference electrode. The potential measurements are then compared against criteria within current industry standards to determine whether or not the structure is adequately protected at the measurement location.

Known methods for monitoring tank cathodic protection systems include permanent, stationary reference electrodes installed within the tanks as well as portable reference electrodes that can be inserted manually into the tank. Both existing methods require a technician be onsite to collect the data utilizing a voltmeter/digital multimeter and either the permanent, stationary reference electrodes fixed at known positions in the tank, or the portable reference electrode.

The permanent, stationary reference electrodes often become contaminated from long-term exposure to the liquid medium within the tank. This contamination lessens the accuracy, consistency, and reliability of the reference electrodes over time. In most cases, portable reference electrodes are utilized in lieu of the permanent, stationary reference electrodes because of this reason. The potential measurements are also a function of the distance between the reference electrode and possible damage on internal coatings adding variability to measurements.

The existing tank cathodic protection system monitoring methods are also limited by lack of access to all of the internal submerged surfaces of the tank. Measurements may often only be collected at specific points within the tank either where the permanent, stationary reference electrodes are installed or where the technician has roof access to lower a portable reference electrode into the tank.

BRIEF SUMMARY OF THE INVENTION

The present invention addresses the above and other needs by providing an automated tank cathodic protection/corrosion monitoring system which includes a mobile Cathodic/Corrosion Protection (CCP) data collection device. The data collection device can be moved horizontally and vertically to different locations in the tank along tank walls and bottom. A reference electrode and corrosion coupon are lowered from the data collection device to desired depths within a liquid medium in the tank to collect data. The data collection device is connected to a programmable, external control unit enabling an operator to program a data collection schedule, the horizontal and vertical distance between readings, a current interruption of the cathodic protection system if the system is designed in a way to handle current interruptions, or interrupting the coupon connection if the system is not designed to handle cathodic protection interruption, and has the ability transmit the data remotely to a control center. These capabilities enable automated, remote monitoring of the CCP system, eliminate the safety concerns associated with sending technicians onto tank roofs, and give a more accurate and complete representation of the CCP system functionality and level of protection achieved.

In accordance with one aspect of the invention, there is provided a data collection device either carried above liquid medium in a tank, or floating on the liquid medium. The data collection device is horizontally positionable and reference electrode and corrosion coupon may be lowered in specified depth intervals, providing data collection over a range of locations in the tank.

In accordance with one aspect of the invention, there is provided a data collection system providing vertical movement of the reference electrode and corrosion coupon allowing the reference electrode and corrosion coupon to be properly stored out of the liquid medium, avoiding probable contamination issues.

BRIEF DESCRIPTION OF THE SEVERAL VIEWS OF THE DRAWING

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing one or more preferred embodiments of the invention. The scope of the invention should be determined with reference to the claims.

Where the terms "about" or "generally" are associated with an element of the invention, it is intended to describe a feature's appearance to the human eye or human perception, and not a precise measurement.

Figure 1:
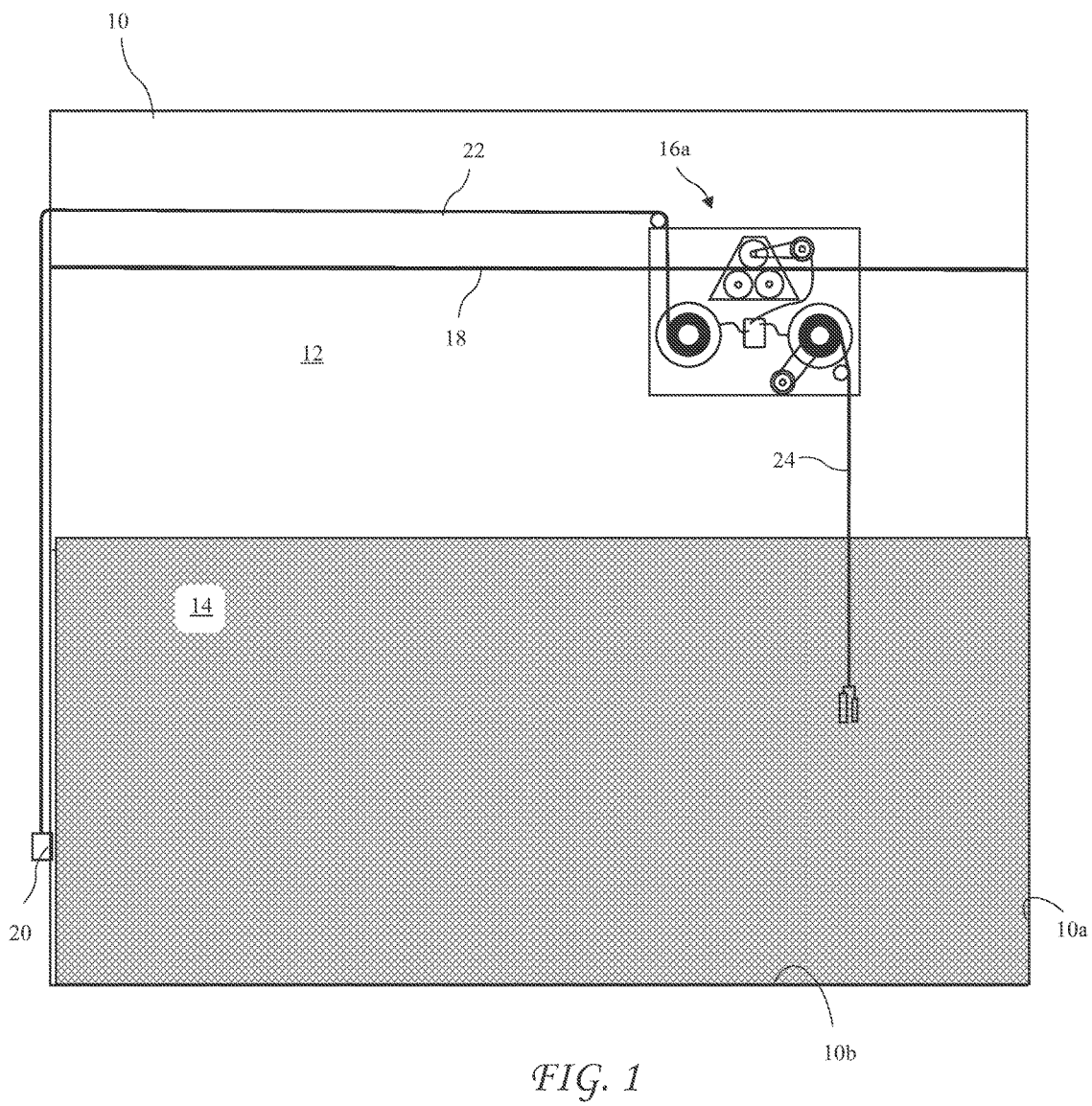
FIG. 1 shows an automated tank cathodic protection/corrosion monitoring system according to the present invention, deployed in a tank.

The present invention is an automated tank cathodic protection/corrosion monitoring system. A first embodiment of a tank 10 Cathodic/Corrosion Protection (CCP) monitoring system is shown in FIG. 1. The CCP monitoring system includes a permanently installed CCP data collection device 16a within the vapor space 12 of the tank 10. The data collection device 16a is carried by a horizontal guide (for example a guide cable) 18 installed within the tank 10, and moves horizontally along the guide cable 18 utilizing an electric DC motor 26 (see FIG. 2). A data and control cable 22 electrically connects the data collection device 16a to a control unit 20 mounted outside the tank 10.

The control unit 20 may include a multifunction interrupter to interrupt either the cathodic protection system or a coupon, a voltage measurement unit, and a data logger unit to record and transfer structure potential and polarized potential measurements. Additionally, the device 16a may employ a second electric DC motor 28 to power vertical movement of a data cable 24 carrying a reference electrode 30 and corrosion coupon 32 (see FIG. 2).

Figure 2:
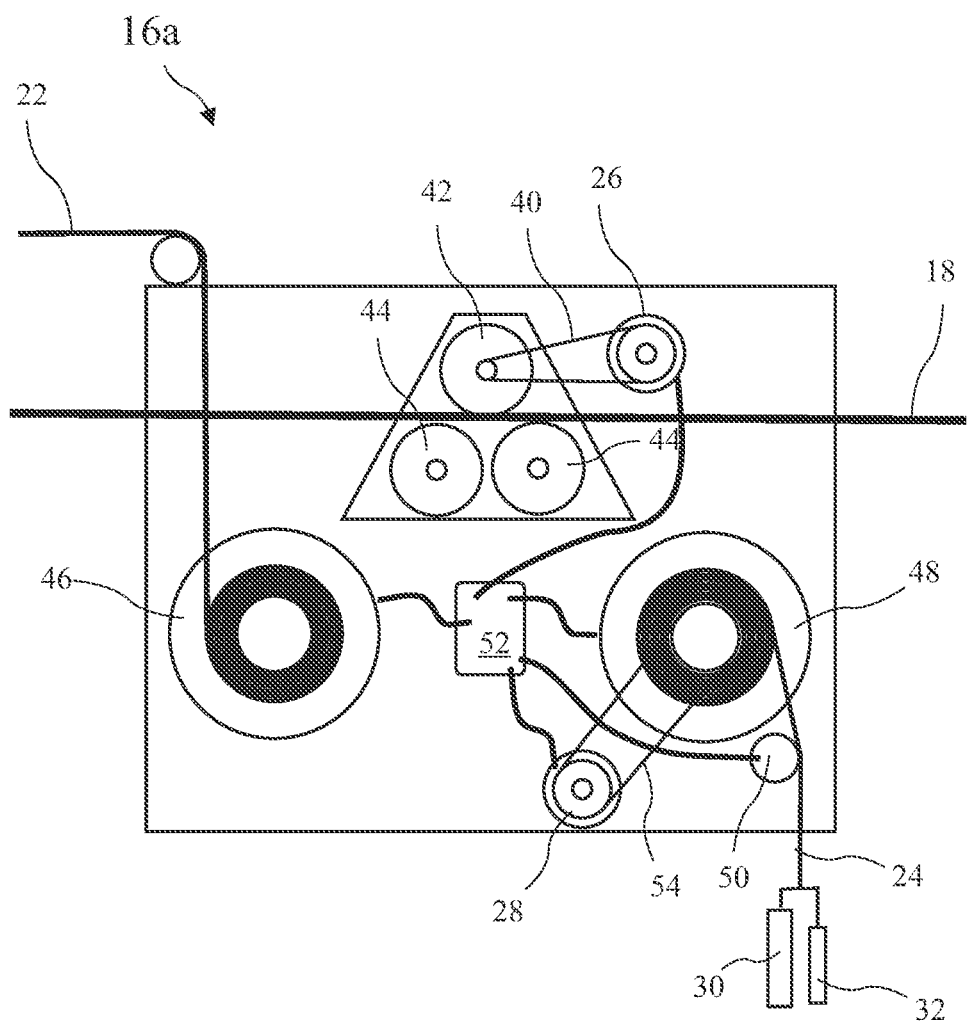
FIG. 2 shows a more detailed view of a mobile data collection device of the automated tank cathodic protection/corrosion monitoring system according to the present invention.

A detailed drawing of the data collection device 16a is shown in FIG. 2. The data collection device 16a is connected to the control unit 20 by the cable 22 to receive commands and provide data. The cable 22 is held on a first reel 46 and is electrically connected to a junction box 52. The junction box 52 is electrically connected to the motor 26 to move the data collection device 16a along the guide cable 18. The motor 26 drives a belt or chain 40 connected to a driven wheel 42. The guide cable 18 is held between the driven wheel 42 and idler wheels 44 to couple the motor 26 to movement of the data collection device 16a.

The junction box 52 is further electrically connected to a second motor 28. The motor 28 drives a second reel 48 through a second belt or chain 54 to raise and lower the cable 24 carrying the reference electrode 30 and corrosion coupon 32 within the tank 10 enabling creation of a complete polarization potential profile along the entire height of the submerged walls 10a and along the entire length of the submerged floor 10b (see FIG. 1). The vertical movement of the reference electrode 30 and corrosion coupon 32 also allows the reference electrode 30 and corrosion coupon 32 to be properly stored out of the liquid medium 14, avoiding probable contamination issues. The data cable 24 runs against cable length counter wheel 50 to accurately measure the depth of the reference electrode 30 and corrosion coupon 32. Additionally, a third motor may drive the reel 46 through a belt or chain, or a spring or similar device may be included in the reel 46 to gather the cable 22 when there is slack in the cable 22.

Figure 3:
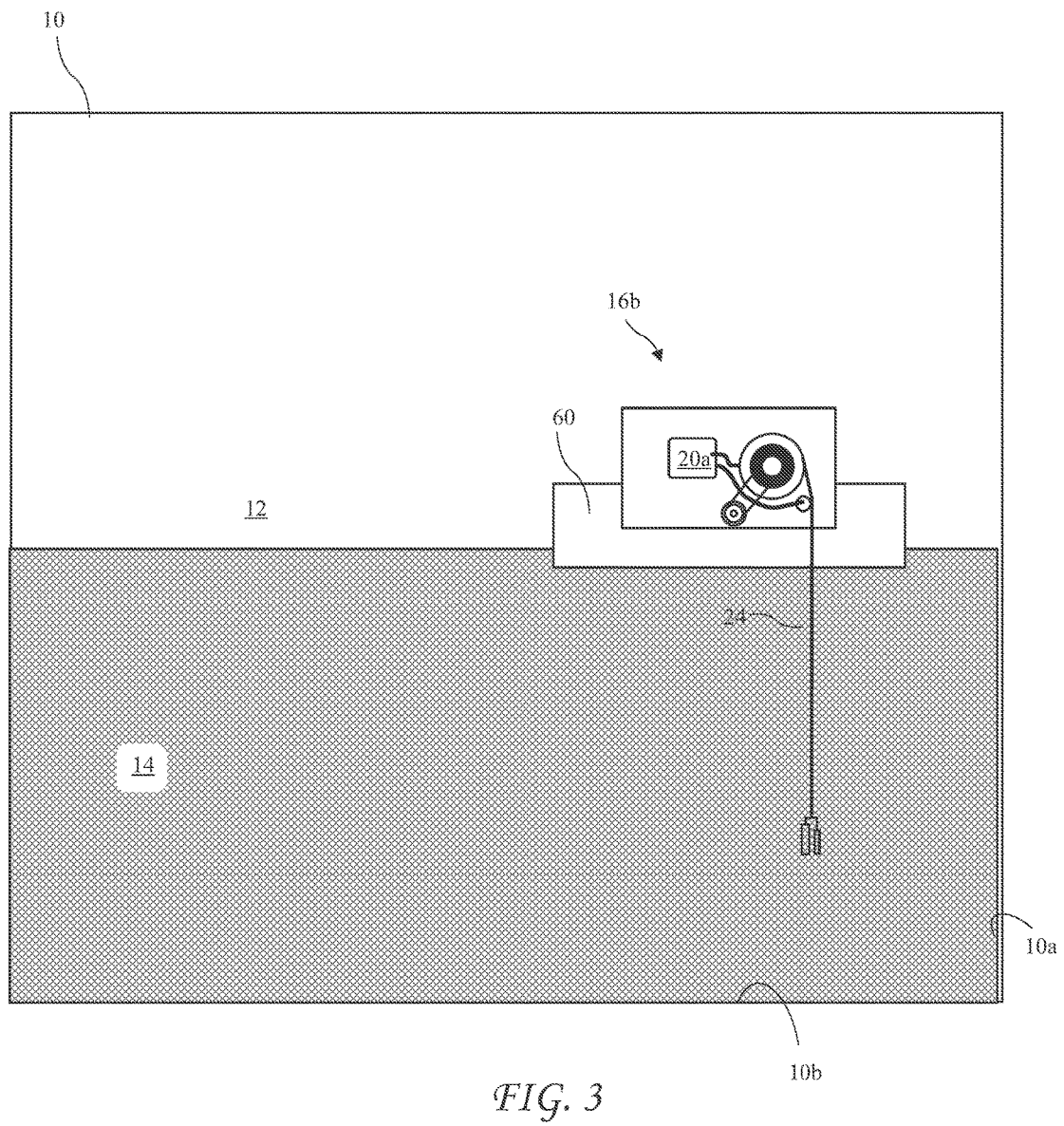
FIG. 3 shows a floating mobile data collection device of the automated tank cathodic protection/corrosion monitoring system according to the present invention.

A second embodiment of a tank CCP monitoring system is shown in FIG. 3. A mobile CCP data collection device 16b floats on top of the liquid medium 14 on a Remotely Operated Vehicle (ROV) or an Autonomous Vehicle (AV) 60. The ROV/AV 60 is free to maneuver horizontally everywhere along the liquid surface for and includes the electric DC motor 28 to power vertical movement of the attached reference electrode 30 and corrosion coupon 32. As in the first embodiment, the ability to move the reference electrode 30 and corrosion coupon 32 horizontally and vertically within the tank 10 will enable the creation of a complete potential profile along the entire height of the submerged walls and along the entire length of the submerged floor. The junction box 52 is replaced by a second control unit 20a. The control unit 20a stores the data collected by the CCP data collection device 16b and/or may remotely transfer the data. After each inspection, the mobile CCP data collection device 16b may be removed from the tank 10 for retrieving the data if the data is not remotely transferred. The mobile CCP data collection device 16b can also be utilized in other submerged marine structure such as jetties, piles and the like.

Both data collection devices 16a and 16b may utilize the corrosion coupon 32 installed in close proximity to the reference electrode 30 and will move concurrently with the reference electrode 30. The corrosion coupon 32 will be made of the same material as the metallic surfaces within the tank 10 or other submerged structures and will represent the uncoated condition of the metallic tank surfaces. The corrosion coupon 32 provides a worst-case scenario for each measurement enabling a more accurate depiction of the level of protection, for example, polarized IR free potential.

Both data collection devices 16a and 16b are connected to a programmable, control unit 20 as seen in FIG. 1. The control unit 20 enables the operator to program a data collection schedule, the horizontal and vertical interval distance between readings, current interruption of the CCP system if the CCP system is designed in a way to handle interruption, and coupon interruption if the system is not designed to handle cathodic protection interruption, and has the ability to transmit the data remotely to a control center. These capabilities enable automated, remote monitoring of the cathodic protection system, eliminate the safety concerns associated with sending technicians onto tank roofs, and give a more accurate, more complete representation of the cathodic protection system functionality and level of protection achieved.

While the invention herein disclosed has been described by means of specific embodiments and applications thereof, numerous modifications and variations could be made thereto by those skilled in the art without departing from the scope of the invention set forth in the claims.

We claim:

1. An automated tank cathodic protection/corrosion monitoring system, comprising:
  a mobile data collection device comprising:
    a vertical data cable;
    a reel releasing and collecting the vertical data cable;
    a reference electrode attached to a lower end of the vertical data cable, the reference electrode configured to provide an accurate voltage measurement;
    a data cable motor connected to a data cable reel to raise and lower the reference electrode in a liquid medium;
    a horizontal guide motor connected to a driven wheel to move the mobile data collection device along a horizontal guide attached to a tank to position the mobile data collection device horizontally; and
    a data and control cable configured to electrically connect the mobile data collection device to a control unit mounted outside the tank, the control unit including:
      a multifunction programmable interrupter to interrupt the current from the cathodic protection system or to a corrosion coupon;
      a voltage measurement unit; and a data logger unit to record and transfer structure potential and polarized potential measurements.

2. An automated tank cathodic protection/corrosion monitoring system, comprising:
water borne vehicle selected from a Remotely Operated Vehicle (ROV) and an Autonomous Vehicle (AV), the water borne vehicle horizontally maneuverable within a tank being monitored to locations for data collection;
a mobile data collection device carried by the water borne vehicle and comprising:
a vertical data cable;
a data cable reel releasing and collecting the vertical data cable into liquid contained in the tank being monitored, portions of the data cable below the water borne vehicle only restrained to reside within tank walls and tank bottom of the tank being monitored;
a reference electrode attached to a lower end of the vertical data cable, the reference electrode configured to provide an accurate voltage measurement;
a data cable motor connected to the data cable reel to raise and lower the reference electrode in a liquid medium; and
a control unit capable of storing data and transmitting data, the control unit including:
a multifunction current interrupter to interrupt current from the cathodic protection system;
a voltage measurement unit;
a data logger unit to record and transfer structure potential and polarized potential measurements; and
a corrosion coupon electrically connected to the control unit.

3. The system of claim 1, wherein the coupon is a corrosion coupon attached to the vertical data cable.

4. The system of claim 3, wherein the multifunction interrupter is configured to interrupt current from the cathodic protection or current provided to the corrosion coupon.

5. The system of claim 2, wherein:
the corrosion coupon is attached to the vertical data cable; and
the multifunction current interrupter is configured to additionally interrupt current provided to the corrosion coupon.

* * * * *